US009974834B2

(12) United States Patent
Gleicher et al.

(10) Patent No.: US 9,974,834 B2
(45) Date of Patent: *May 22, 2018

(54) ADMINISTRATION TO IMPROVE OOCYTE RETRIEVAL PROBABILITIES

(71) Applicants: American Infertility of New York, P.C., New York, NY (US); Norbert Gleicher, New York, NY (US); Vitaly Kushnir, New York, NY (US); David H. Barad, New York, NY (US)

(72) Inventors: Norbert Gleicher, New York, NY (US); Vitaly A. Kushnir, New York, NY (US); David H. Barad, Closter, NJ (US)

(73) Assignee: AMERICAN INFERTILITY OF NEW YORK, P.C., New York, NY (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/060,399

(22) Filed: Mar. 3, 2016

(65) Prior Publication Data

US 2017/0252404 A1     Sep. 7, 2017

(51) Int. Cl.
*A61K 38/18*     (2006.01)
*G01N 33/74*    (2006.01)

(52) U.S. Cl.
CPC ......... *A61K 38/1841* (2013.01); *G01N 33/74* (2013.01); *G01N 2333/495* (2013.01)

(58) Field of Classification Search
None
See application file for complete search history.

(56) References Cited

U.S. PATENT DOCUMENTS

2010/0048525 A1 *   2/2010   Gleicher .............. A61K 31/57
                                                    514/178

OTHER PUBLICATIONS

Gada et al., Fertility and Sterility, 2011 vol. 95, No. 4, Supp. Suppl. 1, pp. S23. Abstract No. P-41.*
Tokuriki and Tawflik, Current Opinion in Structural Biology 2009, 19: 596-604.*
Kong et al., Reproductive Sciences, 2016; 23: 51-60.*
Margolskee and Selgrade, Journal of Theoretical Biology 2013; 326: 21-35.*
Fridén et al., Australian and New Zealand Journal of Obstetrics and Gynaecology 2011; 51: 411-415.*
Gleicher et al., Reproductive Biology and Endocrinology 2010, 8: 64; 7 pages total.*
Blazar et al., Am J Obstet Gynecol. 2011; 205: 223.e1-5.*
Gizzo et al., Reproductive Sciences 2014; 21: 632-639.*
Bhattacharya et al., PLoS ONE 12(3): e0171355. https://doi.org/10.1371/journal.pone.0171355; 22 pages total (Year: 2017).*
Vitaly A. Kushnir, David R. Seifer, David H. Barad, Aritro Sen, Norbert Gleicher, "Potential therapeutic applications of human anti-Müllerian hormone (AMH) analogues in reproductive medicine", accepted for publication Jun. 7, 2017, Springer Science+Business Media LLC, Journal of Assisted Reproduction and Genetics.
Lidija K. Gorsic, Gulum Kosova, Brian Werstein, Ryan Sisk, Richard S. Legro, M. Geoffrey Hayes, Jose M. Teixeira, Andrea Dunaif, Margrit Urbanek, Pathogenic Anti-Müllerian Hormone Variants in Polycystic Ovary Syndrome, Aug. 2017, Journal of Clinical Endocrinology Metabolism, vol. 102(8) pp. 2862-2872.

* cited by examiner

*Primary Examiner* — Christina M Borgeest
(74) *Attorney, Agent, or Firm* — Robert J. Hess; Hess Patent Law Firm

(57) ABSTRACT

A method of diagnosing a subject's percentage of probability of retrieval of oocytes based on an age of the subject by selecting the percentage that matches the subject's AMR level in accord with plotted curves for retrieval of ≥1, ≥2, ≥3, ≥4 and ≥5 oocytes and administering AMR to the subject, as warranted, to increase the AMR level to attain a desired percentage of probability of retrieval of oocytes based upon the age of the subject and in accord with a matching percentage for the increased AMR level from plotted curves for retrieval of ≥1, ≥2, ≥3, ≥4 and ≥5 oocytes.

16 Claims, 5 Drawing Sheets
(5 of 5 Drawing Sheet(s) Filed in Color)

ADMINISTRATION TO IMPROVE OOCYTE RETRIEVAL PROBABILITIES

CROSS-REFERENCE TO COPENDING PATENT APPLICATIONS

U.S. provisional patent application No. 62/128,127 filed Mar. 4, 2015. U.S. utility patent application Ser. No. 15/015,543 filed Feb. 4, 2016.

REFERENCE TO SEQUENCE LISTING SUBMITTED VIA EFS-WEB

This application includes an electronically submitted sequence listing in .txt format. The .txt file contains a sequence listing entitled "CHR-2_ST25.txt" created on Mar. 2, 2018 and is 5,319 bytes in size. The sequence listing contained in this .txt file is part of the specification and is hereby incorporated by reference herein in its entirety.

BACKGROUND OF THE INVENTION

Field of the Invention

One aspect of the invention relates to predicting oocyte retrieval based on probabilities of oocyte numbers in poor prognosis patients with small oocyte yields and the administration of anti-Müllerian hormone (AMH) to such patients accordingly as warranted.

Discussion of Related Art

The small growing follicle pool between primary follicle and small preantral follicle represents the so-called functional ovarian reserve (FOR), which determined oocyte yields in association with in vitro fertilization (IVF). Women who have low FOR (LFOR) in general are poor prognosis patients in IVF, at least partially because they produce small oocyte yield and, therefore, also small embryo numbers (1).

Which LFOR patient could still be encouraged to use own eggs, and which should be directed toward donor eggs has remained controversial. We recently reported in this journal on live birth rates after IVF in very poor prognosis patients, and concluded that, especially in older women, the number of embryos available for transfer is a crucial determinant of outcome (2). Embryo numbers are, however, dependent on oocyte yields, and neither is currently predictable with reasonable accuracy in women with LFOR. The issue is further complicated by ooycte and embryo yields not only being FOR-dependent but also age dependent. A predictive model, therefore, has to consider FOR as well as female age.

At our center, approximately 30% of very poor prognosis patients do not reach embryo transfer (2). Among those, most are cancellations before retrieval and/or after unsuccessful retrievals in which no oocytes were obtained. While cycle costs in such cycles are relatively limited, it would, nevertheless, be desirable to be able to predict with reasonable accuracy probabilities of individual poor prognosis patients to produce oocytes. From the small numbers of likely oocytes in such patients, one then can further assess the likelihood of reaching embryo transfer.

Follicle stimulating hormone (FSH) and anti-Müllerian hormone (AMH) represent FOR, are related to oocyte yields but appear to represent distinctively different components of FOR (3).

The hitherto unanswered question, therefore, arises to what degree these two hormones in women with LFOR at different ages are predictive of small oocyte yields. We previously demonstrated that different combinations of FSH and AMH affect IVF outcomes (3). It, therefore, is likely that these two hormones at different ages may have varying significance in defining FOR and, therefore, oocyte yields.

In order to answer this question, this study assessed age-specific probabilities of retrieving ≥1 to ≥5 oocytes in women with LFOR at different ages based on their FSH and AMH levels.

SUMMARY OF THE INVENTION

This study demonstrates how FSH and AMH in poor prognosis patients with LFOR offer specific probabilities for retrieval of ≥1-≥5 oocytes. Since oocyte numbers reflect on embryo production, and since numbers of transferable embryos in poor prognosis patients predict live birth rates, here published tables should facilitate improved prognostication of poor prognosis patients. This study also suggests that high AMH levels, even better than low FSH levels, appear to compensate for older age, thus raising the possibility that AMH could serve as a therapeutic agent improving oocyte yields.

The study had the objective to determine how much follicle stimulating hormone (FSH) and AMH with low functional ovarian reserve (LFOR) predict oocyte yields at various ages. The design was that of a retrospective cohort study, investigating probability of ≤1 to ≥5 oocytes at ages <35 to ≥43 and the setting was an academically-affiliated private fertility center. The patient(s) in the study were 1554 consecutive mostly poor prognosis patients undergoing fresh non-donor in vitro fertilization (IVF) cycles. The intervention was routine IVF cycles. The main outcome measure(s) were probabilities of retrieval of ≥1-≥5 oocytes at various ages.

At lowest levels (2.5 mIU/mL), FSH at all ages was highly predictable for ≥1 oocyte (88-96%). Probabilities declined and diverged between ages with increasing FSH, though narrowed again at high FSH. AMH demonstrated almost perfect probability for retrieval of ≥1-≥5 oocytes (99-100%) at higher levels (2.5 to ≥5 ng/ml), and at all ages. With declining AMH levels, age categories demonstrated increasingly divergent probabilities, though to lesser degree than FSH.

One aspect of the inventions pertains to obtaining the AMH level of a patient with a conventional AMH test and making a prediction as to the probability of retrieval of ≥1-≥5 oocytes at various ages based on the study.

Another aspect of the invention to administer AMH to raise the AMH level of the patient to such an extent as to obtain a desired percentage probability for the age of the patient that corresponds to the raised AMH level.

BRIEF DESCRIPTION OF THE DRAWING

For a better understanding of the present invention, reference is made to the following description and accompanying drawings, while the scope of the invention is set forth in the appended claims. The patent or application file contains at least one drawing executed in color. Copies of this patent or patent application publication with color drawing(s) will be provided by the Office upon request and payment of the necessary fee.

DISCUSSION OF THE PREFERRED EMBODIMENT

Patients and Hormone Assays

Figure 1:
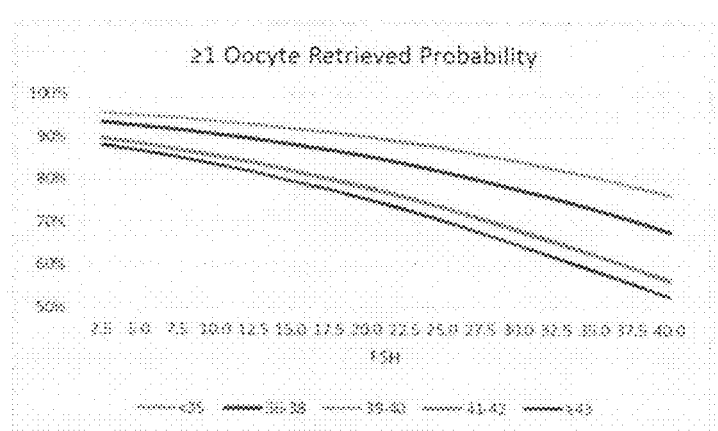
FIG. 1 is a graphical representation of probabilities for retrieval of ≥1 oocyte based upon FSH level from data of Table 1A, with Table 1B demonstrating levels of significance between individual subject age categories.

We investigated 1554 consecutive poor prognosis patients with LFOR. All patient data were extracted from our center's anonymized electronic research data base, representing consecutive IVF cycles. Table 1 summarizes patient characteristics.

TABLE 1

Patient characteristics of study cohort

|  | Median ± 1 interquartile range |
|---|---|
| Age (years) | 40.0 ± 7.0 |
| FSH (mIU/mL) | 11.0 ± 8.0 |
| AMH (ng/mL) | 0.55 ± 1.39 |
| Oocytes (n) | 5.0 ± 9.0 |

As Table 1 demonstrates, based on age (40.0±7.0 years), FSH (11.0±8.0 mIU/mL) and AMH (0.55±1.39 ng/mL) levels, the patient population, indeed, represented a relative poor prognosis patient population with LFOR. Our center clinically defines LFOR as FSH and/or AMH levels outside of the 95th confidence interval for age (1). In here presented study, we, however, defined patients by the percentile in a given age group.

FSH values were tested in house and by commercial assay. Even though at mid-range all commercial AMH assays are similar (variations between assays are usually seen at very low and very high levels), since earlier generation AMH assays differ from the in this study utilized assay, here reported values should not automatically be applied to other AMH assays.

Blood draws occurred at initial presentation to our center, with IVF cycle start on average taking place 8 weeks later.

An AMH test may involve taking a blood sample from the subject in a conventional manner and analyzing the blood sample with appropriate conventional laboratory test procedures and equipment. Laboratory test procedures and equipment to ascertain an AMH level are conventionally known. For example, the Beckman Coulter Diagnostics Access AHM Assay may be used in an analysis to ascertain the AMH level of a subject. According to Beckman Coulter AMH Gen II ELIZA:

> The AMH Gen II ELISA is an enzymatically amplified two-site immunoassay. In the assay, calibrators, controls and samples are incubated in microtitration wells, which have been coated with anti-AMH antibody. After incubation and washing, anti-AMH detection antibody labeled with biotin is added to each well. After a second incubation and washing step, streptavidin-horseradish peroxidase (HRP) is added to the wells. After a third incubation and washing step, the substrate tetramethylbenzidine (TMB) is added to the wells. Lastly, an acidic stopping solution is added. The degree of enzymatic turnover of the substrate is determined by dual wavelength absorbance measurement at 450 nm and between 600 and 630 nm. The absorbance measured is directly proportional to the concentration of AMH in the samples. A set of AMH calibrators is used to plot a calibration curve of absorbance versus AMH concentration. The AMH concentrations in the samples can then be calculated from this calibration curve.

For this invention, AMH was assessed with such Generation II (second generation) assays. Those skilled in the art will understand that other generations of assays and conventional test procedures could be used as well. While AMH assays may vary at the extremes of very high or very low AMH levels, they are very similar in the medium and other ranges significant for this invention and application. As will be disclosed, the previously unknown and undisclosed 'best' AMH ranges of significance for this invention are similar regardless of the assay used.

The AMH levels of Tables 6A, 7A, 8A, 9A and 10A are readily entered and stored in a conventional database, such as within a computer memory or other machine readable medium, in correspondence with the applicable percentage for each age group shown in those tables. Once so stored, any conventional data retrieval program from a database may be used to access the database to identify a match between a given AMH level (i.e., an AMH level of the patient from an AMH test) with the corresponding percentage of probability of retrieval of oocytes. Once such a match of corresponding percentage is made, the corresponding percentage may be displayed or otherwise indicated by a conventional computer-based device and monitor.

In that manner, an indication of the probability for such oocyte retrieval is provided for any applicable one of the oocyte retrieval categories oocytes retrieval, ≥2 oocytes retrieval, ≥3 oocytes retrieval, ≥4 oocytes retrieval, and oocytes retrieval, Alternately, the graphs of FIGS. 6-10 may be retrieved from computer memory for display preferably by matching the applicable one of the graphs with the desired oocytes retrieval (≥1 oocytes retrieval, ≥2 oocytes retrieval, ≥3 oocytes retrieval, ≥4 oocytes retrieval, and ≥5 oocytes retrieval) and then the probability percentage can be matched from the AMH level derived from the AMH test of a subject or patient.

IVF Cycle Protocols

Cycle stimulation protocols at our center are limited, and choice of gonadotropin manufacturer is deferred to patients and their medical insurers. Since most of our center's patients present with LFOR, a majority receive short micro-dose agonist protocols, with FSH (300-450 IU) and human menopausal gonadotropin (hMG, 150 IU). Patients with normal FOR, if under age 38, receive long agonist cycle, including stimulations with 225-300 IU of hMG. Patients with LFOR are pretreated with dehydroepiandrosterone (DHEA) to raise testosterone levels to above 28 ng/mL (1 nmol/L) before IVF cycle start (4), and also receive CoQ10 supplementation (5). Up to age 38, our center transfers in fresh cycles only 1-2 embryos; between ages 38-42, 3 embryos and above age 42, 3 to maximally 5 embryos. Over the last two years, our center progressively also introduced early oocyte retrieval in women with LFOR. Specifically, women with LFOR receive ovulation induction with human chorionic gonadotropin at lead follicle sizes 16-18 mm, rather than the usual 19-22 mm (6).

Embryo Assessment and In Vitro Maturation

Our center routinely transfers embryos on day-3 (cleavage stage) after assessment and grading (7), and also assesses preceding oocyte quality (8). Only 4-8-cell embryos on day-3 of at least grade 3 are transferred or cryopreserved and, therefore, considered good quality. Immature oocytes are, wherever possible in vitro matured over night and fertilized the next day (9).

Statistics

Categorical age with AMH or FSH were used to model the probability of ≥1 to ≥5 oocytes retrieved, using a logistic regression model. Categorical age was contrasted using a Wald chi-square test. All values are presented as median±interquartile range (IQR). A P-value of <0.05 was considered statistically significant. All statistical analyses were performed by the center's senior statistician (S. K. D.), using SAS version 9.4 software.

Results

FIG. 1 presents probabilities for retrieval of ≥1 oocyte. As Table 1A and FIG. 1 demonstrate, at lowest FSH (≤2.5 mIU/mL) probabilities to predict retrieval of at least 1 oocyte are very high at all ages (88% at oldest and 96% at youngest ages). They then decline with rising FSH levels, being only marginally lower at FSH 10.0 mIU/mL (84-94%), at FSH 20.0 mIU/mL 75-90% and, ultimately, at FSH ≥40.0 mIU, generally considered the entry point into menopause, at only 53-76%. Considering that patients with these FSH levels are widely considered to have reached menopause, it is noteworthy that even at oldest investigated ages (≥43 years), 53% of women will still produce ≥1 oocytes.

Table 1B demonstrates the levels of significance between individual age categories, with the maximum difference between youngest and oldest age categories being reached at FSH 52.6 with a 26.2% difference in probability of predicting retrieval of ≥1 oocyte.

Probabilities for retrieval of ≥2, ≥3, ≥4 and ≥5 oocytes are shown in FIGS. 2-5, respectively and tabulated in Tables 2A-5A, with the levels of significance set forth in Table 2B-5B in a manner analogous to that for Table 1B.

The likelihood of 2 oocytes at best FSH levels (≤2.5 mIU/mL) is still excellent at all ages (FIG. 5), ranging from 85% at oldest age to 94% at youngest ages. It declines at FSH of 10.0 mIU/mL to 76-90%, at FSH 20.0 mIU/mL to 58-80% and by menopausal FSH≥40.0 mIU/mL to only 21-40%. Menopausal FSH levels, thus, discriminate quite significantly between likelihood of and oocytes. Table 5C demonstrates levels of significance between age categories, with the largest difference between youngest and oldest categories observed at FSH 30.6 mIU/mL and reaching 26.3%.

Figure 3:
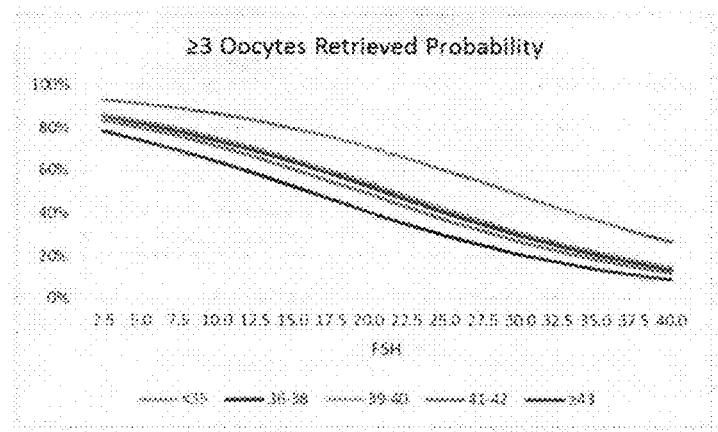
FIG. 3 is a graphical representation of probabilities for retrieval of ≥3 oocyte based upon FSH level from data of Table 3A, with Table 3B demonstrating levels of significance between individual subject age categories.

FIG. 3 and Table 3A summarize probabilities for retrieval of 3 oocytes: Lowest FSH of ≤2.5 mIU/mL offers still very good probabilities of 79% in oldest and 93% in youngest age categories. By FSH 10.0 mIU/mL the range is only 57-83%; by FSH 20.0 mIU/mL, it is 41-71% and by menopausal FSH ≥40.0 mIU/mL in only 9% in the oldest and 27% in the youngest age category. The biggest discrepancy between youngest and oldest groups is seen at FSH 22.8 mIU/mL, reaching 30.9%. Statistical differences between age categories are shown in Table 3B.

Figure 4:
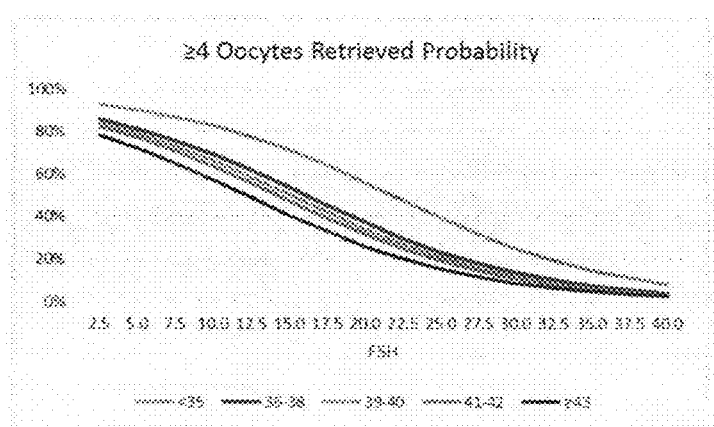
FIG. 4 is a graphical representation of probabilities for retrieval of ≥4 oocyte based upon FSH level from data of Table 4A, with Table 4B demonstrating levels of significance between individual subject age categories.

FIG. 4 and Table 4A demonstrate the same findings in predicting retrieval of 4 oocytes: At FSH ≤2.5 mIU/mL probabilities are between 78-93%; at FSH 10.0 mIU/mL at 57-83%; at FSH 20.0 mIU/mL at 26-56% and at menopausal ≥FSH 40.0 only 2-8%. Table 4B demonstrates continuous loss of significance in difference between age categories 36-42 with increasing oocyte production, while youngest and oldest maintain significant differences, reaching maximum difference at FSH of 17.0 mIU/mL with a 31.1% difference.

Figure 5:
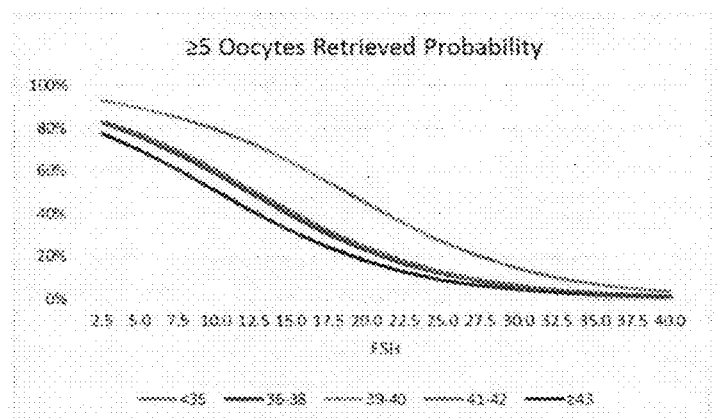
FIG. 5 is a graphical representation of probabilities for retrieval of ≥5 oocyte based upon FSH level from data of Table 5A, with Table 5B demonstrating levels of significance between individual subject age categories.

FIG. 5 and Table 5A summarize probabilities of retrieval of ≥5 oocytes and demonstrate still very reasonable probabilities at lowest FSH of 77-93%; by FSH 10.0 mIU/ml; they, however, have fallen to 51-80%; by FSH 20.0 mIU/mL to 18-45%; and by ≥40.0 mIU/mL to only 1-3%. FIG. 5B demonstrates further disappearance of differences between age categories, with biggest difference between youngest and oldest women reached at FSH level of 14.4%, and representing a 32.1% difference if probability of retrieving 5 oocytes.

FSH, thus, demonstrates best probability at lowest FSH levels, and already by FSH level 10.0 mIU loses significant ability to define probability of numbers of oocytes retrieved. Moreover, while at low FSH levels age plays almost no role in determining probabilities, with increasing FSH age in parallel assumes increasing importance.

Probabilities based on AMH levels are quite different (FIGS. 6-10 and Tables 6A-10A): As all of these figures and tables demonstrate, probabilities of retrieving ≥1 to ≥5 oocytes at highest AMH levels (≥5.0 ng/mL) are identical, and virtually perfect (99-100%), independent of age. This, in itself, is a clear distinction from above discussed FSH probabilities, which even at best (lowest) FSH levels demonstrate a minor degree of age-dependent differences. Indeed, as Tables 6B-10B demonstrate, statistically significant age dependent differences in probabilities were with AMH exceedingly rare, whether in predicting retrieval of ≥1 or ≥5 oocytes. Moreover, even probabilities of ≥5 oocytes, at even lowest AMH levels (≤0.5 ng/mL), were still at 35-52% (FIG. 10).

These data are intriguing because they appear to demonstrate that increasingly high AMH levels in some ways appear to compensate for increasing age when it comes to oocyte production.

We here demonstrated that even in women with LFOR and relatively poor IVF prognoses, FSH and AMH have good utility of assessing the likely probability of how many oocytes a patient may produce in IVF. Moreover, here presented data reconfirm that even in relative poor prognosis patients, up to surprisingly high FSH levels, relative good probabilities of successful oocyte retrieval are maintained and, therefore, the chance for pregnancy and live birth.

These findings correlate well with recently in this journal published IVF outcome data, which demonstrated surprisingly robust live birth rates in highly unfavorable patients at even very advanced ages, as long as they produced minimal numbers of transferrable embryos. Above age 42-43, this meant at least 3 embryos (2).

Since potentially available embryo numbers for transfer are largely dependent on oocyte yields, the ability to establish probabilities for numbers of retrieved oocytes appears of special importance in poor prognosis patients, where, as previously noted, cycle cancellations are relative frequent. Here presented probability tables should facilitate such predictions.

Both hormones do so most specifically at "best" levels, in this study $\leq 2.5$ mIU/mL for FSH, and $\geq 5.0$ ng/mL in AMH. As expected, both measures lose specificity with rising FSH and declining AMH values, though FSH on first impression does so much more profoundly than AMH.

Indeed, it is remarkable how low FSH levels must be ($\leq 2.5$ ng/mL) to show minimal age dependency, a finding congruent with the observation we recently reported that in a regression model, defining clinical pregnancy and live birth rates in IVF based on FSH levels, best rates (i.e., good prognosis) was achieved only at extremely low FSH levels. Even at only mildly higher FSH levels, and still well within what are widely considered normal age-specific FSH levels, pregnancy and live birth rates already clearly declined (2).

Combined these data suggest that, even within so-called normal FSH levels, FSH-dependent components of FOR vary, leading to significant differences in fertility potential of women. In other words, the lower FSH levels are, even within so-called normal range, the better. In this point the study confirms the results of another earlier study from our center, where we investigated FSH and AMH levels in a more general IVF patient population in reference to retrieved oocytes (2). Interestingly, only FSH/oocyte but not AMH/oocyte, was statistically associated with clinical pregnancy chance. Like here, FSH, thus, demonstrated more sensitivity.

This study, thus, reaffirms distinct differences in utility of FSH and AMH and, therefore, further clarifies their respective abilities to define components of FOR: First and foremost, here presented data demonstrate that patient age affects the ability of FSH in determining probabilities of oocyte numbers much more so than does AMH.

AMH between highest levels (2.5-3.0 ng/mL and $\geq 5.0$ ng/mL), indeed, demonstrates practically no age-dependent divergence in probability of retrieving $\geq 1$ to $\geq 5$ oocytes, and only at lower levels starts demonstrating a degree of age-dependent divergence of probabilities, mostly in the oldest patient category of women >43 years.

Figure 2:
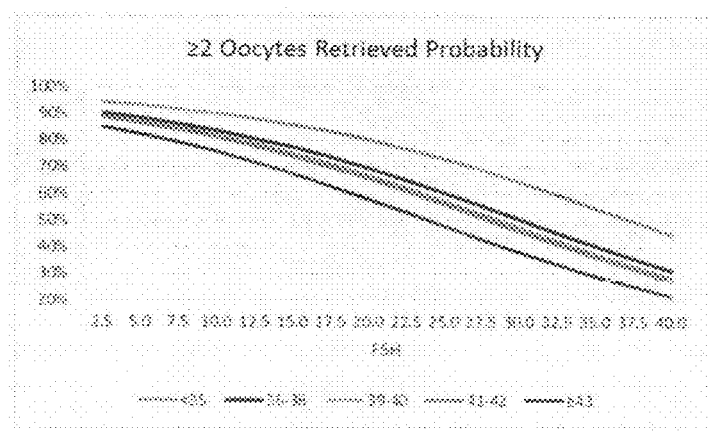
FIG. 2 is a graphical representation of probabilities for retrieval of ≥2 oocyte based upon FSH level from data of Table 2A, with Table 2B demonstrating levels of significance between individual subject age categories.

FSH, in contrast, even at best (lowest) levels, already demonstrates a degree of divergence of age categories, though this divergence progressively increases across increasing categories of retrieved oocytes. Especially once FSH reaches clearly abnormally high FSH levels (at approximately $\leq 10$ mIUI/mL) these age-dependent discrepancies become more easily apparent, with youngest and oldest age categories diverging the most (FIGS. 1 and 2 and Supplemental FIGS. 1-3).

This study, therefore, demonstrates that, ultimately, the meaning of FSH levels is clinically more age-dependent than AMH levels in establishing probabilities of oocyte yields, and offers support for the use of age-dependent FSH assessments, rather than age-independent cut-offs around 10.0-12.0 mIUI, as still widely used in the literature to define LFOR (10).

These findings have clinical relevance in a number of ways: First, they suggest that in determining potential oocyte yields in women with LFOR, utilization of age-specific FSH values (10) is more important than utilization of age-specific AMH (11). They, however, in addition demonstrate that the overall age-dependency of AMH, paradoxically, is more pronounced than that of FSH because only at levels <1.5-2.0 ng/mL does AMH demonstrate a limited ability to differentiate age-dependent probabilities for number of oocytes retrieved. Above those cut off levels, egg production appears virtually age-independent from AMH.

Since AMH at extremely low levels (<0.5 ng/mL) has shown to have very limited predictability in IVF (12), and in this study is demonstrated to have practically no age-dependent predictability for oocyte yields at levels >2.5 ng/ml, prior suggestions that AMH values at very low and very high levels should be interpreted with caution appear confirmed.

Here reported AMH observations, in addition, may point toward potential translational utilization of AMH as a therapeutic agent in female infertility. They suggest that, in contrast to FSH, AMH may have an age-compensating function on ovaries, and especially oocyte production. In other words, these data suggest that in regard to oocyte yields, higher AMH levels may more aggressively be able to compensate for older patient age than lower FSH levels.

This finding concurs with another recent observation made at our center (see U.S. patent application Ser. No. 15/015,543) where, using various prediction models, we demonstrated that "best" AMH levels, compatible with here identified highest AMH levels ($\geq 5.0$ ng/mL), were, even into oldest ages ($\geq 43$ years), strongly associated with unexpectedly high clinical IVF pregnancy rates (13). From that study, it was concluded that AMH at certain peripheral blood levels is associated with significantly improved IVF outcomes and, therefore, should be utilized as a potential therapeutic agent.

Here presented study further expands this observation by suggesting that, at least some of this AMH effect could be an age-negating effect on oocyte yields. That AMH has the potential to effect oocyte yields has recently also been suggested in a mouse model (14). Clearly, the AMH effect at the here identified highest levels, or the "best" AMH levels in U.S. patent application Ser. No. 15/015,543, whose contents are incorporated herein by reference as concerns the "best" AMH levels, is to increase oocyte yields.

In conclusion, this study offers new evidence for differences in how FSH and AMH, at least in women with LFOR, and at different ages, relate to FOR. The study also adds to recent evidence that AMH may at certain peripheral blood levels have anti-aging effects on ovarian function and, therefore, should be investigated as a potential therapeutic agent in IVF. Especially in women with LFOR, AMH may compensate for decreasing oocyte yields with advancing age. Therefore, AMH administration to attain the desired levels will increase oocyte yields based on the results presented.

Finally, it is important to note that here studied patients with LFOR at our center receive a very specific treatment protocol, which involves pretreatment of their ovaries with DHEA (4) and CoQ10 (5) for an average of 6 to 8 weeks, and in recent years oocyte retrieval at much smaller lead follicle sizes than in women with normal FOR (6). While it appears likely that these treatments, which substantially differ from protocols in most other IVF centers for women with LFOR, affected here reported oocyte yields, it seems unlikely that they impacted here reported probabilities. Such a possibility can, however, not be completely ruled out, and here reported results, therefore, should be interpreted with that possibility in mind.

Administration of AMH

If the AMH test of the patient reveals that the AMH level is too low, i.e., beneath the curves of FIGS. 6, 7, 8, 9, or 10 as applies to the oocyte retrieval ($\geq 1$, $\geq 2$, $\geq 3$, $\geq 4$, or $\geq 5$), then AMH may be administered to the patient to raise the AMH level of the patient accordingly. The administration of AMH is discussed in U.S. Ser. No. 15/015,543, whose contents are incorporated herein by reference, which incorporates by reference the contents of U.S. provisional patent application No. 62/128,127 as concerns the contents under the Description on pages 18-65, inclusive in particular of the discussion under the heading "Compositions" on page 21, "Peptides" on pages 21-30, "Nucleic Acids and Vectors" on pages 31-40, "Treatment Methods" on pages 40-43, "Pharmaceutical Compositions and Formulations" on pages 43-56, "Administration/Dosing" on pages 56-61, "Routes of Administration" on pages 61-65, and "Vaginal Administration" on pages 65-66. The manufacture of a composition containing AMH that is described is applicable for use with the present invention and its delivery method and dosages are applicable as well, except that the amount administered over time in accordance with the invention varies, dependent upon the age of the subject, in a manner to raise the AMH level of the patient to fall upon the applicable curve of FIGS. 6, 7, 8, 9 or 10 as applies to the oocyte retrieval ($\geq 1$, $\geq 2$, $\geq 3$, $\geq 4$, or $\geq 5$).

The present invention encompasses treatment of any species of subject, including, but not limited to humans and other primates, mammals, including commercial relevant mammals such a cattle, pigs, horses, sheep, cats, dogs, rats, and mice. The treatment administers to a subject an effective amount of AMH protein to increase the AMH level of the subject to reach the higher AMH level that matches the higher corresponding one of the percentages of retrieval of oocytes based upon the age of the subject. The composition has a peptide that includes an amino acid sequence having at least a 95% identity to SEQ ID NO: 1. The sequence of AMH protein set forth in SEQ ID NO: 1 is found at the paragraph bridging pages 21-22 of provisional application Ser. No. 62/128,127 and copy thereof is supplied herein under the heading SEQUENCE LISTINGS and consists of the same material incorporated by reference into the specification. The reference to 95% identity to SEQ ID NO: 1 is found at p. 32 of provisional application Ser. No. 62/128,127 and is incorporated by reference.

While the foregoing description and drawings represent the preferred embodiments of the present invention, it will be understood that various changes and modifications may be made without departing from the scope of the present invention.

REFERENCES

1. Gleicher N, Weghofer A, Barad D H. Defining ovarian reserve to better understand ovarian aging. Reprod Biol Endocrinol; 2011:9:23
2. Gleicher N, Vega M V, Darmon S K, Weghofer A, Wu Y-G, Wang Q, Zhang L, Albertini D F, Barad D H, Kushnir V A. Live-birth rates in very poor prognosis patients, who are defined as poor responders under the Bologna citeriam with nonelective singe embryo, two-embryo, and three or more embryos transferred. Fertil Steril 2015; 104:1435-1441
3. Gleicher N, Kim A, Weghofer A, Barad D H. Toward a better understanding of functional ovarian reserve: AMH (AMHo) and FSH (FSHo) hormone ratios per retrieved oocytes. J Clin Endocrinol Metab 2012; 97:995-1004.
4. Gleicher N, Barad D H. Dehydroepiandrosterone (DHEA) supplementation in diminished ovarian reserve (DOR). Reprod Bio Endocrinol 2011; 9:67
5. Ben-Meir A, Burstein E, Borrego-Alvarez A, Chong J, Wong E, Yavorska T, Naranian T, Chi M, Wang Y, Bentov Y, Alexis J, Meriano J, Sung H K, Gasser D L, Moley K H, Hekimi S, casper R E, Jurisicova A. Coenzyme Q10 restores oocyte mitochmondrial function and fertility during reproductive aging. Aging cell 2015; 14 (5):887-895
6. Wu Y-G, Barad D H, Kushnit V A, Lazzaroni E, Wang Q, Albertini D F, Gleicher N. Aging-related premature luteinization of granulosa calls is avoided by early oocyte retrieval. J Endocrinol 2015; 226; 167-180
7. Nomura M, Iwase A, Furui K, Kitagawa T, Matsui Y, Yoshikawa M, Kikkawa F. Preferable correlation to blastocyst development and pregnancy rates with a new embryo grading system specific for day 3 embryos. J Assist Reprod Genet 2007; 24:23-28
8. Lazzroni-Tealdi E, Barad D H, Albertini D F, Yu Y, Kushnir V A, Russel H, Wu Y-G, Gleicher N. oocyte scoring enhances embryo scoring in predicting pregnancy chances in IVF where it counts most. PLoS One 10 (12):e0143632
9. Lee H-J, Barad D H, Kushnir V A, Shohat-Tal A, Lazzroni-Tealdi E, Wu Y-G, Gleicher N. Rescue in vtro maturation (IVM) of immature oocytes in stimulated cycles in women with low functional ovarian reserve *LFOR). Endocrine 2015; DOI 10.1007/s12020-015-0744-1
10. Barad D H, Weghofer A, Gleicher N. Age-specific levels for basal follicle-stimulating hormone assessment of ovarian function. Obstet Gynecol 2007; 109 (6):1404-1410
11. Barad D H, Weghofer A, Gleicher N. Utility of age-specific serum anti-Müllerian hormone concentrations. Reprod Biomed Online 2011; 22 (3):284-291
12. Kedem A, Haas J, Geva L L, Yerushalmi G, Gilboa Y, Kanety H, hanochi M, Maman E, Hourvitz A. Ongoing pregnancy rates in women with low and extremely low AMH levels. A multivariate anayis of 769 cycles. PLoS One 2013; 8 (12):e81629
13. Gleicher N, Kushnir V A, Sen A, Darmon S K, Weghofer A, Wu Y-G, Wang Q Zhang L, Albertini D F, Barad D H. Definition b FSH, FSH and embryo numbers of good-, intermediate- and poor-prognosis patients suggests previously unknown IVF outcome-determining factor associated with AMH. Submitted for publication;
14. Hayes E, Kushnir V, Biswas A, Prizani H, Gleicher N, Sen A. Intra-cellular mechanism of anti-Müllerian hormone (AMH) in regulation of follicular development. Submitted for publication

TABLE 1A

| | ≥5 Oocytes Retrieved | | | | |
|---|---|---|---|---|---|
| Max FSH | <35 | 36-38 | 39-40 | 41-42 | ≥43 |
| ≤2.5 | 93% | 82% | 84% | 83% | 77% |
| 5.0 | 90% | 76% | 77% | 77% | 70% |
| 7.5 | 85% | 68% | 70% | 69% | 61% |
| 10.0 | 80% | 59% | 61% | 60% | 51% |
| 12.5 | 73% | 49% | 51% | 50% | 41% |
| 15.0 | 64% | 39% | 41% | 40% | 32% |
| 17.5 | 54% | 30% | 32% | 31% | 24% |
| 20.0 | 45% | 23% | 24% | 24% | 18% |
| 22.5 | 35% | 16% | 18% | 17% | 13% |
| 25.0 | 27% | 12% | 13% | 12% | 9% |
| 27.5 | 20% | 8% | 9% | 9% | 6% |
| 30.0 | 14% | 6% | 6% | 6% | 4% |
| 32.5 | 10% | 4% | 4% | 4% | 3% |
| 35.0 | 7% | 3% | 3% | 3% | 2% |
| 37.5 | 5% | 2% | 2% | 2% | 1% |
| ≥40.0 | 3% | 1% | 1% | 1% | 1% |

TABLE 1B

| | ≥5 Oocyte Retrieved | | | |
|---|---|---|---|---|
| | <35 | 36-38 | 39-40 | 41-42 |
| 36-38 | <0.0001 | | | |
| 39-40 | <0.0001 | 0.7085 | | |
| 41-42 | <0.0001 | 0.7963 | 0.8975 | |
| ≥43 | <0.0001 | 0.0577 | 0.0282 | 0.0282 |

TABLE 2A

| | ≥2 Oocytes Retrieved | | | | |
|---|---|---|---|---|---|
| Max FSH | <35 | 36-38 | 39-40 | 41-42 | ≥43 |
| ≤2.5 | 94% | 90% | 89% | 89% | 85% |
| 5.0 | 93% | 88% | 87% | 87% | 82% |
| 7.5 | 92% | 86% | 85% | 84% | 79% |
| 10.0 | 90% | 84% | 82% | 81% | 76% |
| 12.5 | 88% | 81% | 79% | 78% | 72% |
| 15.0 | 86% | 77% | 75% | 74% | 67% |
| 17.5 | 83% | 74% | 71% | 70% | 63% |
| 20.0 | 80% | 70% | 67% | 66% | 58% |
| 22.5 | 77% | 65% | 62% | 61% | 53% |
| 25.0 | 73% | 60% | 57% | 56% | 48% |
| 27.5 | 69% | 55% | 52% | 51% | 43% |
| 30.0 | 64% | 50% | 47% | 46% | 38% |
| 32.5 | 60% | 45% | 42% | 41% | 33% |
| 35.0 | 55% | 40% | 37% | 36% | 29% |
| 37.5 | 50% | 36% | 33% | 32% | 25% |
| ≥40.0 | 44% | 31% | 29% | 27% | 21% |

TABLE 2B

| | ≥2 Oocyte Retrieved | | | |
|---|---|---|---|---|
| | <35 | 36-38 | 39-40 | 41-42 |
| 36-38 | 0.0232 | | | |
| 39-40 | 0.0073 | 0.6018 | | |
| 41-42 | 0.0024 | 0.4247 | 0.8154 | |
| ≥43 | <0.0001 | 0.0087 | 0.0563 | 0.0708 |

TABLE 3A

| | ≥3 Oocytes Retrieved | | | | |
|---|---|---|---|---|---|
| Max FSH | <35 | 36-38 | 39-40 | 41-42 | ≥43 |
| ≤2.5 | 93% | 86% | 86% | 84% | 79% |
| 5.0 | 91% | 82% | 83% | 80% | 74% |
| 7.5 | 89% | 79% | 80% | 76% | 69% |
| 10.0 | 87% | 74% | 76% | 71% | 64% |
| 12.5 | 84% | 69% | 71% | 66% | 59% |
| 15.0 | 80% | 64% | 66% | 61% | 53% |
| 17.5 | 76% | 59% | 60% | 55% | 47% |
| 20.0 | 71% | 53% | 54% | 49% | 41% |
| 22.5 | 66% | 47% | 48% | 43% | 35% |
| 25.0 | 60% | 41% | 42% | 37% | 30% |
| 27.5 | 55% | 35% | 37% | 32% | 25% |
| 30.0 | 49% | 30% | 31% | 27% | 21% |
| 32.5 | 43% | 25% | 26% | 23% | 17% |
| 35.0 | 37% | 21% | 22% | 19% | 14% |
| 37.5 | 32% | 17% | 18% | 15% | 11% |
| ≥40.0 | 27% | 14% | 15% | 12% | 9% |

TABLE 3B

| | ≥3 Oocyte Retrieved | | | |
|---|---|---|---|---|
| | <35 | 36-38 | 39-40 | 41-42 |
| 36-38 | 0.0004 | | | |
| 39-40 | 0.0018 | 0.7563 | | |
| 41-42 | <0.0001 | 0.4643 | 0.3129 | |
| ≥43 | <0.0001 | 0.0054 | 0.0032 | 0.0439 |

TABLE 4A

| | ≥4 Oocytes Retrieved | | | | |
|---|---|---|---|---|---|
| Max FSH | <35 | 36-38 | 39-40 | 41-42 | ≥43 |
| ≤2.5 | 93% | 86% | 84% | 83% | 78% |
| 5.0 | 90% | 81% | 79% | 77% | 72% |
| 7.5 | 87% | 76% | 73% | 71% | 65% |
| 10.0 | 83% | 69% | 66% | 64% | 57% |
| 12.5 | 78% | 62% | 58% | 56% | 49% |
| 15.0 | 71% | 54% | 50% | 47% | 41% |
| 17.5 | 64% | 45% | 42% | 39% | 33% |
| 20.0 | 56% | 37% | 34% | 32% | 26% |
| 22.5 | 48% | 30% | 27% | 25% | 20% |
| 25.0 | 39% | 23% | 21% | 19% | 15% |
| 27.5 | 32% | 18% | 16% | 15% | 11% |
| 30.0 | 25% | 14% | 12% | 11% | 8% |
| 32.5 | 19% | 10% | 9% | 8% | 6% |
| 35.0 | 15% | 7% | 7% | 6% | 5% |
| 37.5 | 11% | 5% | 5% | 4% | 3% |
| ≥40.0 | 8% | 4% | 3% | 3% | 2% |

TABLE 4B

| | ≥4 Oocyte Retrieved | | | |
|---|---|---|---|---|
| | <35 | 36-38 | 39-40 | 41-42 |
| 36-38 | 0.0004 | | | |
| 39-40 | <0.0001 | 0.5047 | | |
| 41-42 | <0.0001 | 0.1927 | 0.5675 | |
| ≥43 | <0.0001 | 0.0021 | 0.0301 | 0.0977 |

TABLE 5A

| Max FSH | ≥5 Oocytes Retrieved | | | | |
|---|---|---|---|---|---|
| | <35 | 36-38 | 39-40 | 41-42 | ≥43 |
| ≤2.5 | 93% | 82% | 84% | 83% | 77% |
| 5.0 | 90% | 76% | 77% | 77% | 70% |
| 7.5 | 85% | 68% | 70% | 69% | 61% |
| 10.0 | 80% | 59% | 61% | 60% | 51% |
| 12.5 | 73% | 49% | 51% | 50% | 41% |
| 15.0 | 64% | 39% | 41% | 40% | 32% |
| 17.5 | 54% | 30% | 32% | 31% | 24% |
| 20.0 | 45% | 23% | 24% | 24% | 18% |
| 22.5 | 35% | 16% | 18% | 17% | 13% |
| 25.0 | 27% | 12% | 13% | 12% | 9% |
| 27.5 | 20% | 8% | 9% | 9% | 6% |
| 30.0 | 14% | 6% | 6% | 6% | 4% |
| 32.5 | 10% | 4% | 4% | 4% | 3% |
| 35.0 | 7% | 3% | 3% | 3% | 2% |
| 37.5 | 5% | 2% | 2% | 2% | 1% |
| ≥40.0 | 3% | 1% | 1% | 1% | 1% |

TABLE 5B

| | ≥5 Oocyte Retrieved | | | |
|---|---|---|---|---|
| | <35 | 36-38 | 39-40 | 41-42 |
| 36-38 | <0.0001 | | | |
| 39-40 | <0.0001 | 0.7085 | | |
| 41-42 | <0.0001 | 0.7963 | 0.8975 | |
| ≥43 | <0.0001 | 0.0577 | 0.0282 | 0.0282 |

TABLE 6A

| AMH | ≥1 Oocyte Retrieved | | | | |
|---|---|---|---|---|---|
| | <35 | 36-38 | 39-40 | 41-42 | ≥43 |
| ≤0.5 | 84% | 83% | 81% | 79% | 76% |
| 1.0 | 88% | 87% | 86% | 84% | 82% |
| 1.5 | 91% | 91% | 90% | 89% | 86% |
| 2.0 | 94% | 93% | 92% | 92% | 90% |
| 2.5 | 96% | 95% | 95% | 94% | 93% |
| 3.0 | 97% | 97% | 96% | 96% | 95% |
| 3.5 | 98% | 98% | 97% | 97% | 96% |
| 4.0 | 98% | 98% | 98% | 98% | 97% |
| 4.5 | 99% | 99% | 99% | 98% | 98% |
| ≥5.0 | 99% | 99% | 99% | 99% | 99% |

TABLE 6B

| | ≥1 Oocyte Retrieved | | | |
|---|---|---|---|---|
| | <35 | 36-38 | 39-40 | 41-42 |
| 36-38 | 0.8509 | | | |
| 39-40 | 0.5306 | 0.6144 | | |
| 41-42 | 0.3428 | 0.3790 | 0.7198 | |
| ≥43 | 0.0905 | 0.0718 | 0.2150 | 0.3687 |

TABLE 7A

| AMH | ≥2 Oocytes Retrieved | | | | |
|---|---|---|---|---|---|
| | <35 | 36-38 | 39-40 | 41-42 | ≥43 |
| ≤0.5 | 74% | 70% | 73% | 73% | 63% |
| 1.0 | 82% | 79% | 81% | 81% | 73% |
| 1.5 | 88% | 86% | 87% | 87% | 81% |
| 2.0 | 92% | 90% | 91% | 91% | 87% |
| 2.5 | 95% | 94% | 94% | 94% | 92% |

TABLE 7A-continued

| AMH | ≥2 Oocytes Retrieved | | | | |
|---|---|---|---|---|---|
| | <35 | 36-38 | 39-40 | 41-42 | ≥43 |
| 3.0 | 97% | 96% | 96% | 96% | 95% |
| 3.5 | 98% | 97% | 98% | 98% | 97% |
| 4.0 | 99% | 98% | 99% | 99% | 98% |
| 4.5 | 99% | 99% | 99% | 99% | 99% |
| ≥5.0 | 99% | 99% | 99% | 99% | 99% |

TABLE 7B

| | ≥2 Oocyte Retrieved | | | |
|---|---|---|---|---|
| | <35 | 36-38 | 39-40 | 41-42 |
| 36-38 | 0.4750 | | | |
| 39-40 | 0.7740 | 0.6278 | | |
| 41-42 | 0.7371 | 0.6476 | 0.9624 | |
| ≥43 | 0.0524 | 0.1559 | 0.0500 | 0.0431 |

TABLE 8A

| AMH | ≥3 Oocytes Retrieved | | | | |
|---|---|---|---|---|---|
| | <35 | 36-38 | 39-40 | 41-42 | ≥43 |
| ≤0.5 | 64% | 55% | 62% | 59% | 50% |
| 1.0 | 76% | 69% | 75% | 72% | 64% |
| 1.5 | 85% | 80% | 84% | 83% | 77% |
| 2.0 | 91% | 88% | 91% | 90% | 86% |
| 2.5 | 95% | 93% | 95% | 94% | 92% |
| 3.0 | 97% | 96% | 97% | 97% | 95% |
| 3.5 | 98% | 98% | 98% | 98% | 97% |
| 4.0 | 99% | 99% | 99% | 99% | 99% |
| 4.5 | 100% | 99% | 99% | 99% | 99% |
| ≥5.0 | 100% | 100% | 100% | 100% | 100% |

TABLE 8B

| | ≥3 Oocyte Retrieved | | | |
|---|---|---|---|---|
| | <35 | 36-38 | 39-40 | 41-42 |
| 36-38 | 0.1905 | | | |
| 39-40 | 0.7305 | 0.2733 | | |
| 41-42 | 0.4590 | 0.4889 | 0.6550 | |
| ≥43 | 0.0198 | 0.2808 | 0.0197 | 0.0517 |

TABLE 9A

| AMH | ≥4 Oocytes Retrieved | | | | |
|---|---|---|---|---|---|
| | <35 | 36-38 | 39-40 | 41-42 | ≥43 |
| ≤0.5 | 57% | 46% | 49% | 48% | 42% |
| 1.0 | 70% | 60% | 63% | 62% | 56% |
| 1.5 | 81% | 72% | 75% | 74% | 70% |
| 2.0 | 88% | 82% | 84% | 84% | 80% |
| 2.5 | 93% | 89% | 90% | 90% | 88% |
| 3.0 | 96% | 94% | 94% | 94% | 93% |
| 3.5 | 98% | 96% | 97% | 97% | 96% |
| 4.0 | 99% | 98% | 98% | 98% | 97% |
| 4.5 | 99% | 99% | 99% | 99% | 99% |
| ≥5.0 | 100% | 99% | 99% | 99% | 99% |

TABLE 9B

| | ≥4 Oocyte Retrieved | | | |
|---|---|---|---|---|
| | <35 | 36-38 | 39-40 | 41-42 |
| 36-38 | 0.0851 | | | |
| 39-40 | 0.2227 | 0.5829 | | |
| 41-42 | 0.1731 | 0.6585 | 0.8994 | |
| ≥43 | 0.0127 | 0.4821 | 0.1830 | 0.2106 |

TABLE 10A

| | ≥5 Oocytes Retrieved | | | | |
|---|---|---|---|---|---|
| AMH | <35 | 36-38 | 39-40 | 41-42 | ≥43 |
| ≤0.5 | 52% | 37% | 43% | 45% | 35% |
| 1.0 | 65% | 51% | 57% | 59% | 49% |
| 1.5 | 76% | 64% | 69% | 71% | 62% |
| 2.0 | 85% | 76% | 80% | 81% | 74% |
| 2.5 | 91% | 84% | 87% | 88% | 83% |
| 3.0 | 94% | 90% | 92% | 93% | 89% |

TABLE 10A-continued

| | ≥5 Oocytes Retrieved | | | | |
|---|---|---|---|---|---|
| AMH | <35 | 36-38 | 39-40 | 41-42 | ≥43 |
| 3.5 | 97% | 94% | 95% | 96% | 94% |
| 4.0 | 98% | 97% | 97% | 97% | 96% |
| 4.5 | 99% | 98% | 98% | 99% | 98% |
| ≥5.0 | 99% | 99% | 99% | 99% | 99% |

TABLE 10B

| | ≥5 Oocyte Retrieved | | | |
|---|---|---|---|---|
| | <35 | 36-38 | 39-40 | 41-42 |
| 36-38 | 0.0259 | | | |
| 39-40 | 0.1821 | 0.3360 | | |
| 41-42 | 0.3293 | 0.1513 | 0.6609 | |
| ≥43 | 0.0045 | 0.6574 | 0.1225 | 0.0329 |

---

SEQUENCE LISTING

<160> NUMBER OF SEQ ID NOS: 1

<210> SEQ ID NO 1
<211> LENGTH: 560
<212> TYPE: PRT
<213> ORGANISM: Homo sapiens

<400> SEQUENCE: 1

```
Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
                20                  25                  30

Gly Thr Ser Gly Leu Ile Phe Arg Glu Asp Leu Asp Trp Pro Pro Gly
            35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
                100                 105                 110

Pro Ser Leu Arg Arg Leu Gly Ala Trp Leu Arg Asp Pro Gly Gly Gln
            115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
                180                 185                 190

Thr Arg Tyr Leu Val Leu Ala Val Asp Arg Pro Ala Gly Ala Trp Arg
            195                 200                 205

Gly Ser Gly Leu Ala Leu Thr Leu Gln Pro Arg Gly Glu Asp Ser Arg
    210                 215                 220
```

-continued

```
Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Arg Pro
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Lys Ala Leu Gln
            420                 425                 430

Gly Leu Arg Val Glu Trp Arg Gly Arg Asp Pro Arg Gly Pro Gly Arg
        435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
    530                 535                 540

Ser Ala His His Val Pro Asn Met Val Ala Thr Glu Cys Gly Cys Arg
545                 550                 555                 560
```

Figure 6:
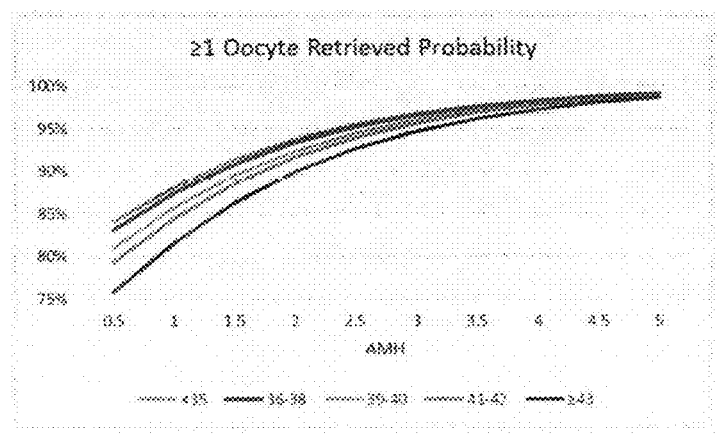
FIG. 6 is a graphical representation of probabilities for retrieval of ≥1 oocyte based upon AMH level from data of Table 6A, with Table 6B demonstrating levels of significance between individual subject age categories.
Figure 7:
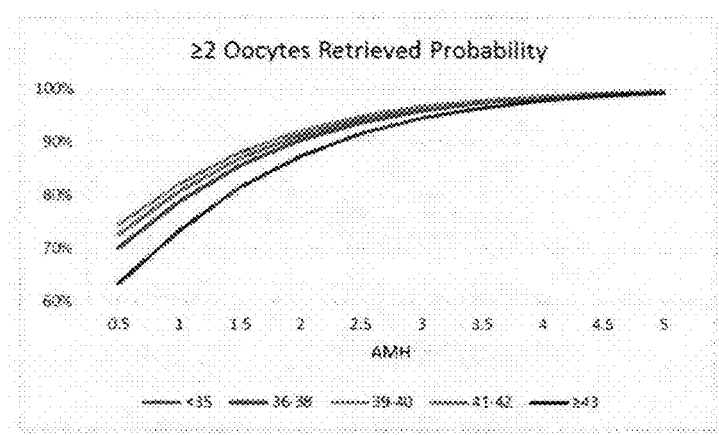
FIG. 7 is a graphical representation of probabilities for retrieval of ≥2 oocyte based upon FSH level from data of Table 7A, with Table 7B demonstrating levels of significance between individual subject age categories.
Figure 8:
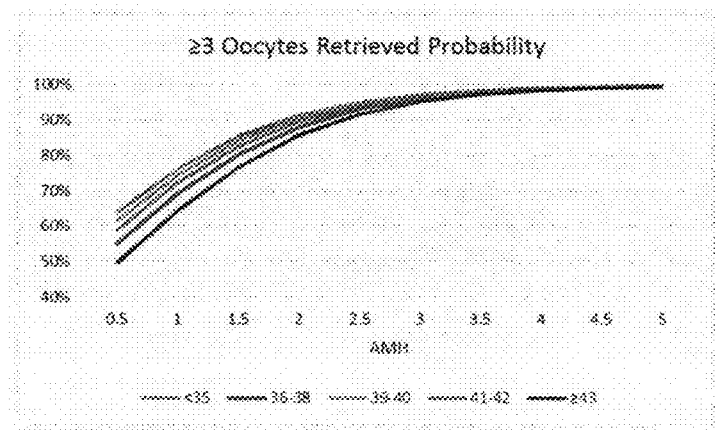
FIG. 8 is a graphical representation of probabilities for retrieval of ≥3 oocyte based upon FSH level from data of Table 8A, with Table 8B demonstrating levels of significance between individual subject age categories.
Figure 9:
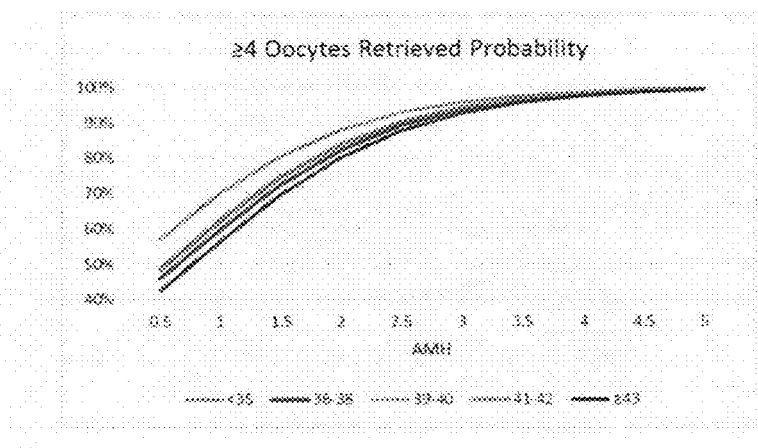
FIG. 9 is a graphical representation of probabilities for retrieval of ≥4 oocyte based upon FSH level from data of Table 9A, with Table 9B demonstrating levels of significance between individual subject age categories.
Figure 10:
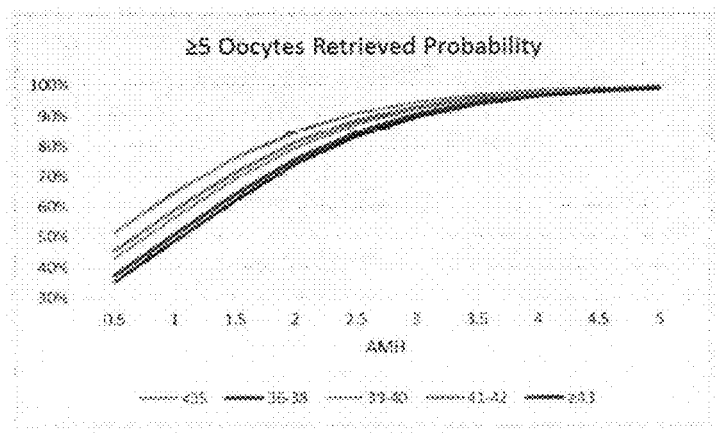
FIG. 10 is a graphical representation of probabilities for retrieval of ≥5 oocyte based upon FSH level from data of Table 10A, with Table 10B demonstrating levels of significance between individual subject age categories.

What is claimed is:

1. A method of correlating percentage of retrieval of oocytes with an increase in anti-Müllerian hormone (AMH), comprising:

matching a higher AMH level with a higher corresponding one of percentages of retrieval of oocytes based upon an age of the subject in accordance with the applicable plotted curve of:

FIG. 6 for retrieval of ≥1 oocytes;

FIG. 7 for retrieval of ≥2 oocytes;

FIG. 8 for retrieval of ≥3 oocytes;

FIG. 9 for retrieval of ≥4 oocytes; and

FIG. 10 for retrieval of ≥5 oocytes; and administering to the subject a composition having an effective amount of AMH protein to increase the AMH level of the subject to reach the higher AMH level that matches the higher corresponding one of the percentages of retrieval of oocytes based upon the age of the subject, wherein the composition has a peptide comprising an amino acid sequence having at least a 95% identity to SEQ ID NO: 1.

2. The method of claim 1, in combination with increasing a pregnancy rate in the subject, wherein the administering includes administering to the subject an effective amount of the AMH protein in the composition to achieve and maintain the AMH level of between 3.5-8.5 ng/ml within the subject.

3. The method of claim 2, wherein the administering occurs for a period of time selected from the group consisting of about 1 day to about 180 days, 10 days to about 120 days and 30 days to about 90 days, and at dosages within a range selected from the group consisting of about 100 ng per day to about 44,000 ng per day, and about 22,000 ng per day to about 44,000 ng per day.

4. The method of claim 2, wherein the administering to the subject an effective amount of the AMH protein in the composition to achieve and maintain the AMH level within a range of:
   3.5-8.5 ng/ml for the subject under 36 years old;
   4.5-7.5 ng/ml for the subject 36-38 years old inclusive;
   5.0-7.0 ng/ml for the subject 39-42 years old inclusive; and
   4.5-7.5 ng/ml for the subject over 42 years old.

5. The method of claim 2, further comprising adjusting, over time, the effective amount of the AMH protein in the composition being administered accordingly to maintain the AMH level of between 3.5-8.5 ng/ml within the subject through testing of the AMH level of the patient over time.

6. The method of claim 2 in combination with increasing a live birth rate in the subject, further comprising administering to the subject an effective amount of AMH to achieve and maintain the AMH level over time of between:
   5.0-6.5 ng/ml inclusive for the subject who is between 39-42 years old,
   4.5-6.5 ng/ml inclusive for the subject who is between 36-38 years old, and
   3.5-7.0 ng/ml for the subject who is under 36 years old.

7. The method of claim 2 in combination with increasing a live birth rate in a subject, comprising administering to the subject an effective amount of the AMH protein in the composition to achieve and maintain an AMH level within a range of:
   3.5-7.0 ng/ml for the subject under 36 years old; and
   4.0-6.5 ng/ml for the subject 36-42 years old inclusive.

8. The method of claim 7, wherein the administering occurs for a period of time selected from the group consisting of about 1 day to about 180 days, 10 days to about 120 days and 30 days to about 90 days, and at dosages within a range selected from the group consisting of about 100 ng per day to about 44,000 ng per day, and about 22,000 ng per day to about 44,000 ng per day.

9. A method that is based upon a correspondence between an anti-Müllerian hormone (AMH) level of a subject and probability of retrieval of oocytes from the subject, comprising:
   ascertaining the AMH level of the subject by taking a blood sample of the subject, incubating the blood sample in an assay in a manner to measure absorbance, and calculating the AMH level based on the measured absorbance, which is directly proportional to AMH concentration in the blood sample;
   matching an increase in the AMH level of the subject with a corresponding one of percentages of retrieval of oocytes based upon an age of the subject in accord with an applicable plotted curve of:
   FIG. 6 for retrieval of ≥1 oocytes;
   FIG. 7 for retrieval of ≥2 oocytes;
   FIG. 8 for retrieval of ≥3 oocytes;
   FIG. 9 for retrieval of ≥4 oocytes; and
   FIG. 10 for retrieval of ≥5 oocytes; and
   administering a composition having an effective amount of AMH protein to a subject to increase the AMH level of the subject to the increase in the AMH level that matches the corresponding one of the percentages of retrieval of oocytes that is based upon the age of the subject,
   wherein the composition has a peptide comprising an amino acid sequence having at least a 95% identity to SEQ ID NO: 1.

10. The method of claim 9, in combination with increasing a pregnancy rate in the subject, wherein the administering includes administering to the subject an effective amount of the AMH protein in the composition to achieve and maintain the AMH level of between 3.5-8.5 ng/ml within the subject.

11. The method of claim 10, wherein the administering occurs for a period of time selected from the group consisting of about 1 day to about 180 days, 10 days to about 120 days and 30 days to about 90 days, and at dosages within a range selected from the category consisting of about 100 ng per day to about 44,000 ng per day, and about 22,000 ng per day to about 44,000 ng per day.

12. The method of claim 10, wherein the administering to the subject an effective amount of the AMH protein to achieve and maintain the AMH level is within a range of:
   3.5-8.5 ng/ml for the subject under 36 years old;
   4.5-7.5 ng/ml for the subject 36-38 years old inclusive;
   5.0-7.0 ng/ml for the subject 39-42 years old inclusive; and
   4.5-7.5 ng/ml for the subject over 42 years old.

13. The method of claim 10, further comprising adjusting, over time, the effective amount of the AMH protein in the composition being administered accordingly to maintain the AMH level of between 3.5-8.5 ng/ml within the subject through testing of the AMH level of the patient over time.

14. The method of claim 10 in combination with increasing a live birth rate in the subject, further comprising administering to the subject an effective amount of the AMH protein in the composition to achieve and maintain the AMH level over time of between:
   5.0-6.5 ng/ml inclusive for the subject who is between 39-42 years old,
   4.5-6.5 ng/ml inclusive for the subject who is between 36-38 years old, and
   3.5-7.0 ng/ml for the subject who is under 36 years old.

15. The method of claim 10 in combination with increasing a live birth rate in a subject, comprising administering to the subject an effective amount of the AMH protein in the composition to achieve and maintain an AMH level within a range of:
   3.5-7.0 ng/ml for the subject under 36 years old; and
   4.0-6.5 ng/ml for the subject 36-42 years old inclusive.

16. The method of claim 15, wherein the administering occurs for a period of time selected from the group consisting of about 1 day to about 180 days, 10 days to about 120 days and 30 days to about 90 days, and at dosages within a range selected from the group consisting of about 100 ng per day to about 44,000 ng per day, and about 22,000 ng per day to about 44,000 ng per day.

* * * * *

UNITED STATES PATENT AND TRADEMARK OFFICE
CERTIFICATE OF CORRECTION

PATENT NO. : 9,974,834 B2
APPLICATION NO. : 15/060399
DATED : May 22, 2018
INVENTOR(S) : Norbert Gleicher, Vitaly Kushnir and David H. Barad Page 1 of 1

It is certified that error appears in the above-identified patent and that said Letters Patent is hereby corrected as shown below:

On the Title Page

Replace the title with the following amended title:
ANTI- MÜLLERIAN HORMONE (AMH) ADMINISTRATION TO IMPROVE OOCYTE RETRIEVAL PROBABILITIES Replace the abstract with the following amended abstract:
A method of diagnosing a subject's percentage of probability of retrieval of oocytes based on an age of the subject by selecting the percentage that matches the subject's AMH level in accord with plotted curves for retrieval of $\geq 1$, $\geq 2$, $\geq 3$, $\geq 4$ and $\geq 5$ oocytes and administering AMH to the subject, as warranted, to increase the AMH level to attain a desired percentage of probability of retrieval of oocytes based upon the age of the subject and in accord with a matching percentage for the increased AMH level from plotted curves for retrieval of $\geq 1$, $\geq 2$, $\geq 3$, $\geq 4$ and $\geq 5$ oocytes.

Signed and Sealed this
Eleventh Day of June, 2019

Andrei Iancu
*Director of the United States Patent and Trademark Office*